United States Patent
Knudson et al.

(10) Patent No.: US 7,146,981 B2
(45) Date of Patent: *Dec. 12, 2006

(54) PHARYNGEAL WALL TREATMENT

(75) Inventors: Mark B. Knudson, Shoreview, MN (US); Timothy R. Conrad, Eden Prairie, MN (US)

(73) Assignee: Restore Medical, Inc., St. Paul, MN (US)

( * ) Notice: Subject to any disclaimer, the term of this patent is extended or adjusted under 35 U.S.C. 154(b) by 563 days.

This patent is subject to a terminal disclaimer.

(21) Appl. No.: 10/066,967

(22) Filed: Feb. 4, 2002

(65) Prior Publication Data

US 2003/0149445 A1 Aug. 7, 2003

(51) Int. Cl.
*A61F 5/56* (2006.01)

(52) U.S. Cl. .................................................... 128/848

(58) Field of Classification Search .............. 606/196, 606/204.45; 128/898, 848
See application file for complete search history.

(56) References Cited

U.S. PATENT DOCUMENTS

| | | | |
|---|---|---|---|
| 3,998,209 A | 12/1976 | Macvaugh | |
| 4,553,540 A * | 11/1985 | Straith | 128/200.26 |
| 4,803,075 A | 2/1989 | Wallace et al. | |
| 4,830,008 A | 5/1989 | Meer | |
| 4,978,323 A | 12/1990 | Freedman | |
| 5,046,512 A | 9/1991 | Murchie | |
| 5,052,409 A | 10/1991 | Tepper | |
| 5,133,354 A | 7/1992 | Kallok | |
| 5,158,080 A | 10/1992 | Kallok | |
| 5,176,618 A | 1/1993 | Freedman | |
| 5,178,156 A | 1/1993 | Takishima et al. | |
| 5,190,053 A | 3/1993 | Meer | |
| 5,204,382 A | 4/1993 | Wallace et al. | |
| 5,258,028 A | 11/1993 | Ersek et al. | |
| 5,284,161 A | 2/1994 | Karell | |
| 5,421,406 A | 6/1995 | Furusawa et al. | |
| 5,443,063 A * | 8/1995 | Greenberg | 128/207.15 |
| 5,456,662 A | 10/1995 | Edwards et al. | |
| 5,494,029 A | 2/1996 | Lane et al. | |
| 5,514,131 A | 5/1996 | Edwards et al. | |
| 5,540,733 A | 7/1996 | Testerman et al. | |
| 5,591,216 A | 1/1997 | Testerman et al. | |
| 5,669,377 A | 9/1997 | Fenn | |
| 5,674,191 A | 10/1997 | Edwards et al. | |
| 5,718,702 A | 2/1998 | Edwards | |

(Continued)

FOREIGN PATENT DOCUMENTS

DE 44 12 190 A1 10/1995

(Continued)

OTHER PUBLICATIONS

Aboubakr, S. et al., "Long-term facilitation in obstructive sleep apnea patients during NREM sleep", *J Appl Physiol*, vol. 91, pp. 2751-2757 (Dec. 2001).

(Continued)

*Primary Examiner*—(Jackie) Tan-Uyen T. Ho
(74) *Attorney, Agent, or Firm*—Merchant & Gould P.C.

(57) ABSTRACT

A patient's pharyngeal wall is treated by inserting an expander member into the airway and positioning an active portion of the expander member in opposition to portions of the pharyngeal wall to be treated. The expander member is activated to urge the wall portions outwardly to an outwardly displaced position. The expander member is then deactivated while leaving the wall portions in the outwardly placed position and the expander member is removed from said airway. A further aspect of the treatment includes stabilization of at least a portion of the pharyngeal wall after compression of portions of the wall.

13 Claims, 20 Drawing Sheets

U.S. PATENT DOCUMENTS

| | | | |
|---|---|---|---|
| 5,791,341 | A | 8/1998 | Bullard |
| 5,792,067 | A | 8/1998 | Karell |
| 5,792,478 | A | 8/1998 | Lawin et al. |
| 5,843,021 | A | 12/1998 | Edwards et al. |
| 5,853,004 | A | 12/1998 | Goodman |
| RE36,120 | E | 3/1999 | Karell |
| 5,897,579 | A | 4/1999 | Sanders |
| 5,922,006 | A | 7/1999 | Sugerman |
| 5,979,456 | A | 11/1999 | Magovern |
| 5,983,136 | A | 11/1999 | Kamen |
| 5,988,171 | A | 11/1999 | Sohn et al. |
| 6,098,629 | A | 8/2000 | Johnson et al. |
| 6,161,541 | A * | 12/2000 | Woodson .................... 128/848 |
| 6,216,702 | B1 | 4/2001 | Gjersøe |
| 6,240,316 | B1 | 5/2001 | Richmond et al. |
| 6,250,307 | B1 | 6/2001 | Conrad et al. |
| 6,431,174 | B1 * | 8/2002 | Knudson et al. ............ 128/898 |
| 6,636,767 | B1 * | 10/2003 | Knudson et al. .............. 607/42 |
| 6,748,950 | B1 | 6/2004 | Clark et al. |
| 2004/0045556 | A1 | 3/2004 | Nelson et al. |
| 2004/0134491 | A1 | 7/2004 | Pflueger et al. |

FOREIGN PATENT DOCUMENTS

| | | |
|---|---|---|
| DE | 199 20 114 A1 | 11/2000 |
| EP | 0 706 808 A1 | 4/1996 |
| EP | 1 039 859 B1 | 12/2003 |
| JP | 11-33120 | 9/1999 |
| SU | 1553140 A1 | 3/1990 |
| WO | WO 01/19301 A1 | 3/2001 |
| WO | WO 01/23039 A1 | 4/2001 |

OTHER PUBLICATIONS

Badr, M. "Effect of ventilatory drive on upper airway patency in humans during NREM sleep", Respiration Physiology, vol. 103, No. 1, pp. 1-10 (1996).

Boot, H. et al., "Long-Term Results of Uvulopalatopharyngoplasty for Obstructive Sleep Apnea Syndrome", Laryngoscope, vol. 110, pp. 469-475 (Mar. 2000).

Boudewyns, A. et al., "Temperature-controlled Radiofrequency Tissue Volume Reduction of the Soft Palate (Somnoplasty®) in the Treatment of Habitual Snoring: Results of a European Multicenter Trial", Acta Otolaryngol, vol. 120, pp. 981-985 (2000).

Brietzke, S. et al., "Injection snoreplasty: How to treat snoring without all the pain and expense", Otolaryngology-Head and Neck Surgery, pp. 503-510 (May 2001).

Cole, P. et al., Review Article "Snoring: A Review and a Reassessment", The Journal of Otolaryngology, vol. 24, No. 5, pp. 303-306 (1995).

Coleman, S.et al., "Midline radiofrequency tissue reduction of the palate for bothersome snoring and sleep-disordered breathing: A clinical trial", Otolaryngology Head and Neck Surgery, vol. 122, No. 3, pp. 387-394 (Mar. 2000).

Collard, P. et al., "Why Should We Enlarge the Pharynx in Obstructive Sleep Apnea?", Sleep, vol. 19, No. 9, pp. S85-S87 (1996).

Courey, M. et al., "Histologic and Physiologic Effects of Electrocautery, $CO_2$ Laser, and Radiofrequency Injury in the Porcine Soft Palate", Laryngoscope, vol. 109, pp. 1316-1319 (Aug. 1999).

Dalmasso, F. et al., "Snoring: analysis, measurement, clinical implications and applications", European Respiratory Journal, vol. 9, pp. 146-159 (1996).

Dreher, A. et al., "Nasenatmungsbehinderung und schlafbezogene Atmungsstorungen", Laryngo-Rhino-Otol, vol. 78, pp. 313-317 (1999).

Ellis, P. et al., "Surgical relief of snoring due to palatal flutter: a preliminary report", Annals of the Royal College of Surgeons of England, vol. 75, pp. 286-290 (1993).

Fischer, Y. et al., "Die Radiofrequenzablation des weichen Gaumens (Somnoplastik)", HNO, vol. 1, pp. 33-40 (2000).

Gillette, P. et al., "Pediatric Cardiac Pacing", Cardiology Clinics, vol. 10, No. 4, pp. 749-754 (Nov. 1992).

Harries, P. et al., "Review Article The surgical treatment of snoring", Journal of Laryngology and Otology, vol. 110, pp. 1105-1106 (Dec. 1996).

Huang, L., "Flutter of Cantilevered Plates in Axial Flow", Journal of Fluids and Structures, vol. 9, pp. 127-147 (1995).

Huang, L. et al., "Biomechanics of snoring", 5 pages, (Source Unknown) (Date Unknown).

Hukins, C. et al., "Radiofrequency Tissue Volume Reduction of the Soft Palate in Simple Snoring", Arch Otolaryngol Head Neck Surgery, vol. 126, pp. 602-606 (May 2000).

Li, K. et al., "Radiofrequency volumetric reduction of the palate: An extended follow-up study", Otolaryngology Head and Neck Surgery, vol. 122, No. 3, pp. 410-414 (Mar. 2000).

LaFrentz et al., "Palatal Stiffening Techniques for Snoring in a Novel Canine Model", Abstracts of the Twenty-Second Annual Mid Winter Research Meeting of the Association for Research in Otolaryngology, Abstract No. 499, vol. 22, pp. 125-126 (Feb. 13-19, 1999).

Lemperle, G. et al., "PMMA Microspheres (Artecoll) for Skin and Soft-Tissue Augmentation. Part II: Clinical Investigations", Plastic and Reconstructive Surgery, vol. 96, No 3, pp. 627-634 (Sep. 1995).

Littlefield, P. et al., "Snoring surgery: Which is best for you?", ENT-Ear, Nose, & Throat Journal, vol. 78, No. 11, pp. 861-870 (Nov. 1999).

Lorenz, C., "If he snores—what can you do about it?", Today's Woman, 2 pgs, (Jul. 1948).

Mair, E. et al., "Cautery-assisted palatal stiffening operation", Otolaryngology Head and Neck surgery, vol. 122, No. 4, pp. 547-555 (Apr. 2000).

Nutrition for Life International Brochure, "Snoreless™-A Natural Lubricant That Really Works!", 2 pages (Dec. 1999).

Our Health News Brochure, "Snore-Free Nights Guaranteed!", 2 pages (Date Unknown).

Phillips, M., "Stenting therapy for stenosing airway diseases", Respirology, vol. 3, pp. 215-219 (1998).

Schwab, R. et al., "Dynamic upper airway imaging during awake respiration in normal subjects and patients with sleep disordered breathing", AM Rev Respir Dis, vol. 148, pp. 1385-1398 (1993).

Schwab, R., "Upper Airway Imaging", Clinics in Chest Medicine, vol. 19, No. 1, pp. 33-54 (Mar. 1998).

Schwab, R. et al., "Upper airway and soft tissue anatomy in normal subjects and patients with sleep-disordered breathing", Am Journal of Respir Crit Care Med, vol. 152, pp. 1673-1689 (1995).

Schwartz, R. et al., "Effects of electrical stimulation to the soft palate on snoring and obstructive sleep apnea", Journal of Prosthetic Dentistry, vol. 76, No. 3, pp. 273-281 (Sep. 1996).

Schwartz, A., "Pharyngeal Airway Obstruction in Obstructive Sleep Apnea", Otolaryngologic Clinics of North America, vol. 31, No. 6, pp. 911-918 (Dec. 1998).

Sher, A. et al., "The Efficacy of Surgical Modifications of the Upper Airway in Adults With Obstructive Sleep Apnea Syndrome", Sleep, vol. 19, No. 2, pp. 156-177 (1996).

Somnoplasty Brochure, "Haven't you suffered from snoring long enough", 2 pages (Date Unknown).

SNAP Brochure, "Our Siagnostic Procedures are a Snap!", Snap Laboratories Glenview, IL, 4 pages (Date Unknown).

Stauffer, J. et al., "Pharyngeal Size and Resistance in Obstructive Sleep Apnea", Amer Rev of Respir Disease, vol. 136, No. 3, pp. 622-627 (Sep. 1987).

Wheatley, J. et al., "Mechanical properties of the upper airway", Pulmonary Med, vol. 4, pp. 363-369 (1998).

Wiltfang, J. et al., "First results on daytime submandibular electrostimulation of suprahyoidal muscles to prevent night-time hypopharyngeal collapse in obstructive sleep apnea syndrome", Intl Journ of Oral & Maxillofacial Surgery, vol. 28, pp. 21-25 (1999).

Winter, W. et al., "Enlargement of the lateral pharyngeal fat pad space in pigs increases upper airway resistance", Amer Physiological Society, pp. 726-731 (1995).

Blumen et al., Radiofrequency Ablation for the Treatment of Mild to Moderate Obstructive Sleep Apnea, Nov. 2002; pp. 2086-2092.

Ersek et al., "Minimally Invasive Macro Implants," Worldplast, vol. 1, No. 4, pp. 275-285 (1996).

* cited by examiner

US 7,146,981 B2

PHARYNGEAL WALL TREATMENT

BACKGROUND

1. Field of the Invention

This invention is directed to methods and apparatuses for treating the pharyngeal wall of a patient. More particularly, this invention pertains to method and apparatus for treating a pharyngeal wall area as part of a sleep apnea treatment.

2. Description of the Prior Art

Sleep apnea and snoring are complex phenomena. Commonly assigned U.S. Pat. No. 6,250,307 describes various prior techniques and discloses a novel treatment for such conditions (including a permanent palatal implant).

These prior art teachings include Huang, et al., "Biomechanics of Snoring", Endeavour, p. 96–100, Vol. 19, No. 3 (1995). That publication estimates that up to 20% of the adult population snores habitually. Snoring can be a serious cause of marital discord. In addition, snoring can present a serious health risk to the snorer. In 10% of habitual snorers, collapse of the airway during sleep can lead to obstructive sleep apnea syndrome. Id. In addition to describing a model for palatal flutter, that publication also describes a model for collapse of the pharyngeal wall.

Notwithstanding efforts have been made to treat snoring and sleep apnea. These include palatal treatments such as electrical stimulation of the soft palate. See, e.g., Schwartz, et al., "Effects of electrical stimulation to the soft palate on snoring and obstructive sleep apnea", J. Prosthetic Dentistry, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime submandibular electrostimulation of suprahyoidal muscles to prevent night-time hypopharyngeal collapse in obstructive sleep apnea syndrome", International Journal of Oral & Maxillofacial Surgery, pp. 21–25 (1999).

Surgical treatments for the soft palate have also been employed. One such treatment is uvulopalatopharyngoplasty (UPPP) where about 2 cm of the trailing edge of the soft palate is removed to reduce the soft palate's ability to flutter between the tongue and the pharyngeal wall of the throat. See, Huang, et al., supra at 99 and Harries, et al., "The Surgical treatment of snoring", Journal of Laryngology and Otology, pp. 1105–1106 (1996) which describes removal of up to 1.5 cm of the soft palate. Assessment of snoring treatment is discussed in Cole, et al., "Snoring: A review and a Reassessment", Journal of Otolaryngology, pp. 303–306 (1995). Huang, et al., propose an alternative to UPPP which proposal includes using a surgical laser to create scar tissue on the surface of the soft palate. The scar is to reduce flexibility of the soft palate to reduce palatal flutter. RF ablation (so-called Somnoplasty as advocated by Somnus Technologies) is also suggested to treat the soft palate. RF ablation has also been suggested for ablation of the tongue base.

In pharyngeal snoring and sleep apnea, the pharyngeal airway collapses in an area between the soft palate and the larynx. One technique for treating airway collapse is continuous positive airway pressure (CPAP). In CPAP air is passed under pressure to maintain a patent airway. However, such equipment is bulky, expensive and generally restricted to patients with obstructive sleep apnea severe enough to threaten general health. Huang, et al. at p. 97.

Treatments of the pharyngeal wall include electrical stimulation is suggested in U.S. Pat. No. 6,240,316 to Richmond et al. issued May 29, 2001, U.S. Pat. No. 4,830,008 to Meer issued May 16, 1989, U.S. Pat. No. 5,158,080 to Kallok issued Oct. 27, 1992, U.S. Pat. No. 5,591,216 to Testerman et al. issued Jan. 7, 1997 and PCT International Publication No. WO 01/23039 published Apr. 5, 2001 (on PCT International Application No. PCT/US00/26616 filed Sep. 28, 2000 with priority to U.S. Ser. No. 09/409,018 filed Sep. 29, 1999). U.S. Pat. No. 5,979,456 to Magovern dated Nov. 9, 1999 teaches an apparatus for modifying the shape of a pharynx. These teachings include a shape-memory structure having an activated shape and a quiescent shape. Dreher et al., "Influence of nasal obstruction on sleep-associated breathing disorders", So. Laryngo-Rhino-Otologie, pp. 313–317 (June 1999), suggests using nasal stents to treat sleep associated breathing disorders involving nasal obstruction. Upper airway dilating drug treatment is suggested in Aboubakr, et al., "Long-term facilitation in obstructive sleep apnea patients during NREM sleep", J. Applied Physiology, pp. 2751–2757 (December 2001).

Surgical treatments for sleep apnea are described in Sher et al., "The Efficacy of Surgical Modifications of the Upper Airway in Adults with Obstructive Sleep Apnea Syndrome", Sleep, Vol. 19, No. 2, pp. 156–177 (1996). Anatomical evaluation of patients with sleep apnea or other sleep disordered breathing are described in Schwab, et al., "Upper Airway and Soft Tissue Anatomy in Normal Subjects and Patients with Sleep-Disordered Breathing", Am. J. Respir. Crit. Care Med., Vol. 152, pp. 1673–1689 (1995) ("Schwab I") and Schwab et al., "Dynamic Upper Airway Imaging During Awake Respiration in Normal Subjects and Patients with Sleep Disordered Breathing", Am. Rev. Respir. Dis., Vol. 148, pp. 1385–1400 (1993) ("Schwab II). In Schwab I, it is noted that apneic patients have a smaller airway size and width and a thicker lateral pharyngeal wall. For reviews of pharyngeal wall thickness and other structure and obstructive sleep apnea, see, also, Wheatley, et al., "Mechanical Properties of the Upper Airway", Current Opinion in Pulmonary Medicine, pp. 363–369 (November 1998); Schwartz et al., "Pharyngeal airway obstruction in obstructive sleep apnea: pathophysiology and clinical implication", Otolaryngologic Clinics of N. Amer., pp. 911–918 (December 1998); Collard, et al., "Why should we enlarge the pharynx in obstructive sleep apnea?", Sleep, (9 Suppl.) pp. S85–S87 (November 1996); Winter, et al., "Enlargement of the lateral pharyngeal fat pad space in pigs increases upper airway resistance", J. Applied Physiology, pp. 726–731 (September 1995); and Stauffer, et al., "Pharyngeal Size and Resistance in Obstructive Sleep Apnea", Amer. Review of Respiratory Disease, pp. 623–627 (September 1987)

SUMMARY OF THE INVENTION

According to one aspect of the present invention, methods and apparatuses are disclosed for treating a pharyngeal airway having a pharyngeal wall of a patient at least partially surrounding and defining said airway. The method includes inserting an expander member into the airway and positioning an active portion of the expander member in opposition to portions of the wall to be treated. The expander member is activated to urge the wall portions outwardly to an outwardly displaced position. The expander member is then deactivated while leaving the wall portions in the outwardly placed position and the expander member is removed from said airway. A further aspect of the invention includes stabilization of at least a portion of the pharyngeal wall in the outwardly placed position after compression of portions of the wall.

DESCRIPTION OF THE PREFERRED EMBODIMENT

A. Physiology Background

Referring now to the several drawing figures, in which identical elements are numbered identically throughout, a description of a preferred embodiment of the present invention will now be provided.

The disclosures of U.S. Pat. No. 6,250,307 and PCT International Publication No. WO 01/19301 (PCT/US00/40830) are incorporated herein by reference.

Figure 1:
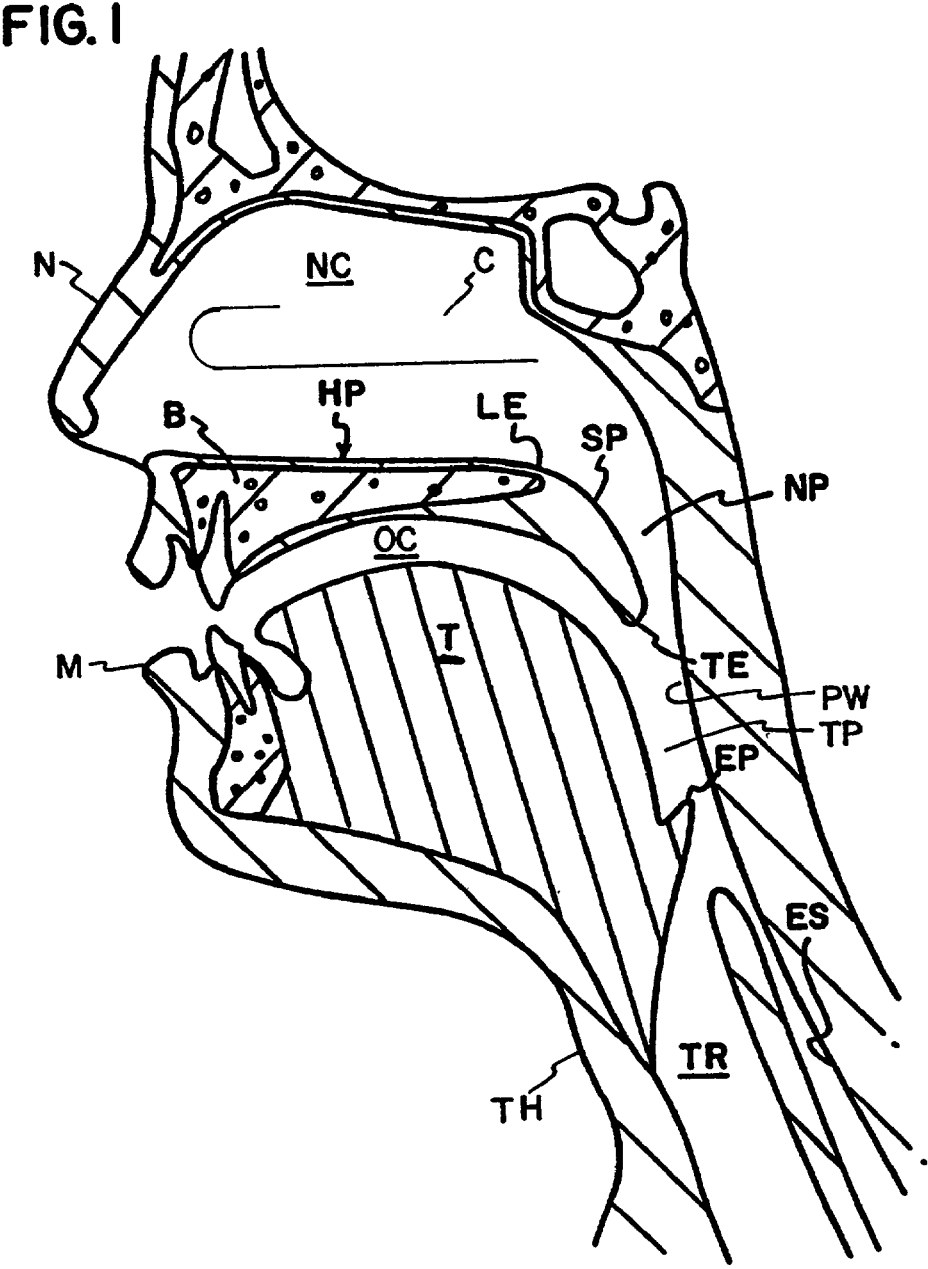
FIG. 1 shows, in cross-section, a naso-pharyngeal area of an untreated patient.

FIG. 1 shows, in cross-section, a naso-pharyngeal area of an untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area of the patient (defining, in part, the pharyngeal airway PA in FIGS. 5 and 13) with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Snoring can result from vibration of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds. It is not uncommon for vibratory action from more than one region of the naso-pharyngeal area to contribute to snoring sounds. Sleep apnea can result from partial or full collapse of the naso-pharyngeal wall during sleep.

Figure 5:
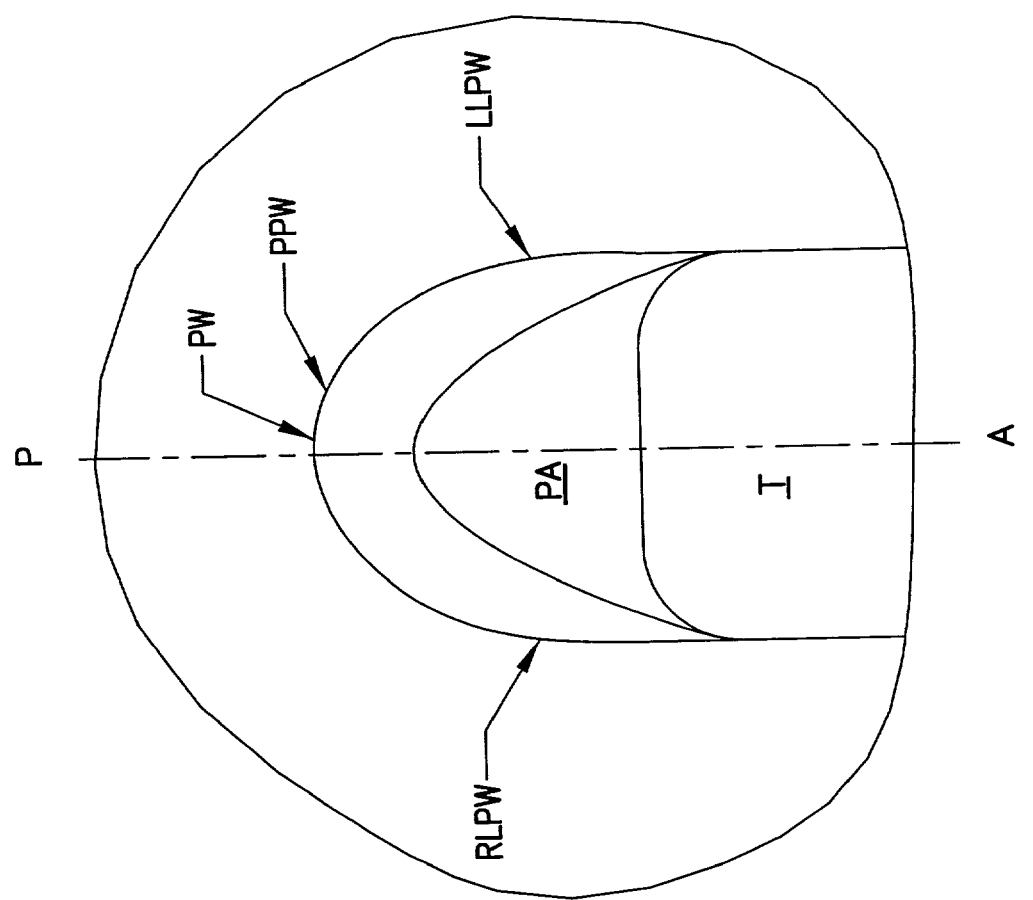
FIG. 5 is a schematic cross-sectional view (taken generally along line 5—5 in FIG. 2) of a pharyngeal airway at a position in a person with the airway defined by opposing portions of a pharyngeal wall and a base of a tongue.

FIG. 5 shows a schematic representation of a cross-section of a throat with the pharyngeal airway PA defined by the pharyngeal wall PW and the tongue T. The anterior-posterior axis is labeled AP to assist in discerning the orientation. The pharyngeal wall PW is shown as including the left lateral pharyngeal wall LLPW, right lateral pharyngeal wall RLPW and posterior pharyngeal wall PPW.

B. Disclosure of Prior Application

Figure 2:
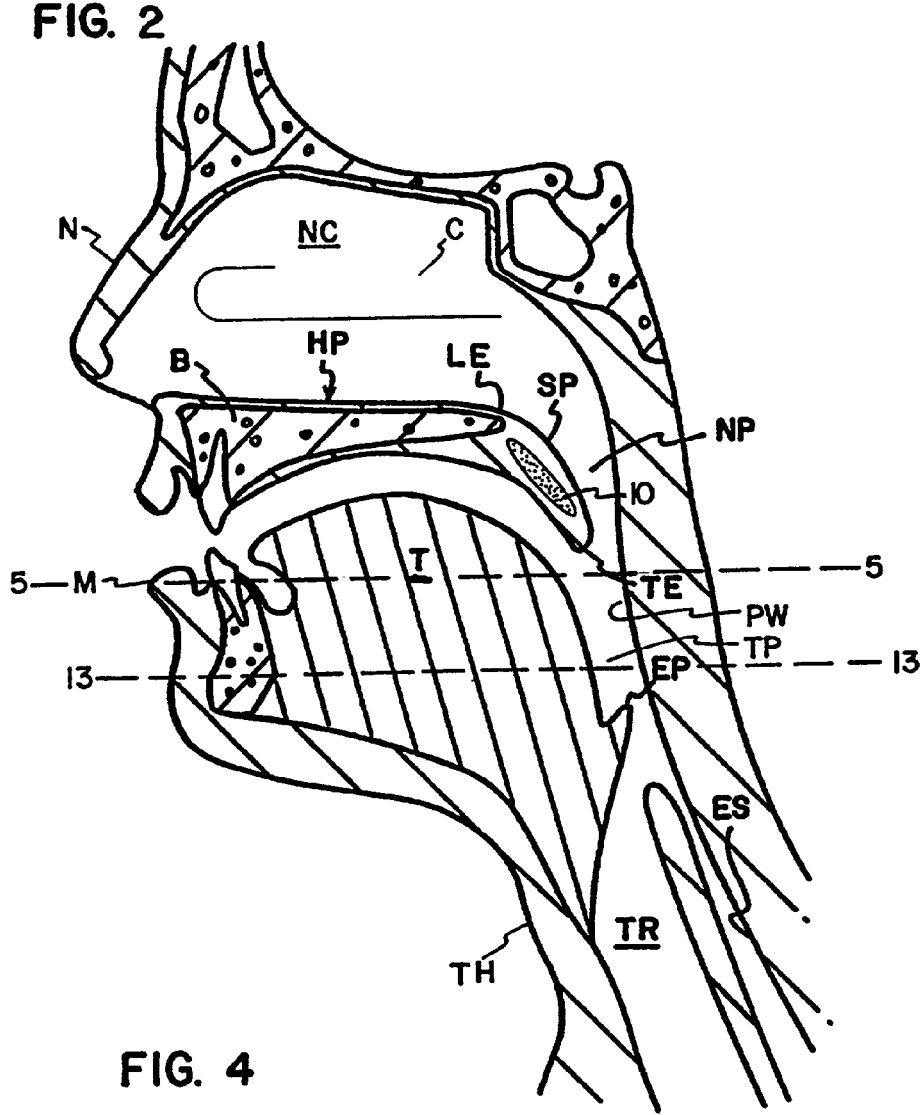
FIG. 2 is the view of FIG. 1 with the soft palate containing an implant in the form of a bolus of micro-beads deposited in a linear path.
Figure 3:
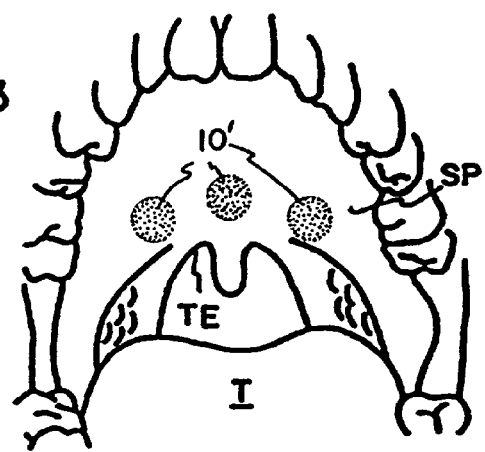
FIG. 3 is a frontal view of the patient of FIG. 3 showing an alternative embodiment with micro-beads deposited as spherical deposits.

In addition to disclosing the teachings of U.S. Pat. No. 6,250,307 and the teachings of selected embodiments of PCT International Publication No. WO 01/19301 (both incorporated herein by reference), commonly assigned and co-pending patent application U.S. Ser. No. 09/636,803, filed Aug. 10, 2000, which is hereby incorporated by reference in its entirety, describes techniques for stiffening tissue of the pharyngeal airway with a bolus of particulate matter. FIGS. 2 and 3 show are taken from the '803 application and show an implant 10 as a bolus of particulate matter. An example of such particulate matter would be micro-beads. An example of such is taught in U.S. Pat. Nos. 5,792,478 and 5,421,406. These patents teach carbon-coated metallic or ceramic particles having cross-sectional dimensions of between 100 and 1,000 microns. The particles are carried in a fluid or gel. These patents state that upon insertion into body tissue, the particles do not migrate significantly and, apparently due to fibrotic response, the tissue into which the particles are injected stiffens.

The particles of U.S. Pat. Nos. 5,792,478 and 5,421,406 are one example of particles for stiffening injection. Such particles can also include ceramic particles or pure carbon or other bio-compatible particles. The particles can be carried in a liquid or gel medium. The particles can have multi-modal particle size distributions (i.e., a mix of two or more sizes of particles with the smaller particles filling interstitial spaces between larger particles).

The bolus 10 of particles can be applied by a needle to inject the bolus 10 into the soft palate SP. The bolus can be the same volume as the volume of the implants 20 of FIGS. 8 and 9 of U.S. Pat. No. 6,250,307. With reference to FIG. 3, a multiple of bolus injections can be made in the soft palate resulting in deposition of generally spherical deposits 10' of particles. Alternatively, an injecting needle can be withdrawn while simultaneously ejecting particles for the bolus 10 (FIG. 2) to be deposited in a line similar in dimensions to the implants 20 of FIGS. 8 and 9 of U.S. Pat. No. 6,250,307.

The foregoing emphasizes the use of implants to stiffen the soft palate SP. Implants 10 can be placed in any of the tissue of the naso-pharyngeal area (e.g., the concha C, soft palate SP or pharyngeal wall PW) to treat snoring. Also, such a treatment can stiffen the tissue of the throat and treat sleep apnea resulting from airway collapse by stiffening the airway.

Figure 4:
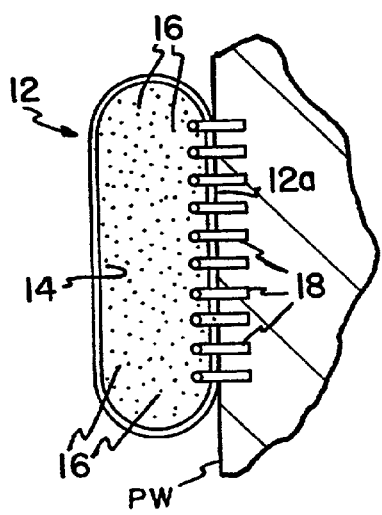
FIG. 4 is a schematic representation showing a patch for delivering a bolus of micro-beads through a plurality of needles.

While a needle deposition of a bolus of particles may be preferred, the bolus can be applied in other manners. FIG. 4 (which is a reproduction of FIG. 16 of the '803 application) illustrates deposition of particulates through a patch 12 having a volume 14 containing such micro-beads 16.

One side 12a of the patch 12 contains an array of micro-needles 18 communicating with the volume 14. The needles 18 may be small diameter, shallow penetration needles to minimize pain and blood. Examples of shallow, small diameter needles are shown in U.S. Pat. No. 5,582,184 to Erickson et al. Placing the surface 12a against the tissue (e.g., the pharyngeal wall PW as shown in FIG. 4), the needles 18 penetrate the outer surface of the tissue PW. The patch 12 can then be compressed (by finger pressure, roller or the like) to eject the beads 16 from the volume 14 through the plurality of needles 18. The patch 12 can be provided with interior dividing walls (not shown) so that some of the volume of beads 16 is ejected through each needle 18. The side 12a acts as a stop surface to ensure control over the penetration depth of the needles 18 to reduce risk of undesired puncture of underlying structures.

Stiffening of the naso-pharyngeal tissue provides structure to reduce vibration and snoring. Such structure reduces airway collapse as a treatment for sleep apnea.

C. Pharyngeal Wall Compression

FIGS. 5–16 show various methods and apparatus for enlarging the pharyngeal airway PA. As will be described, further disclosure is made for stiffening the tissue or maintaining the enlarged airway size.

Figure 6:
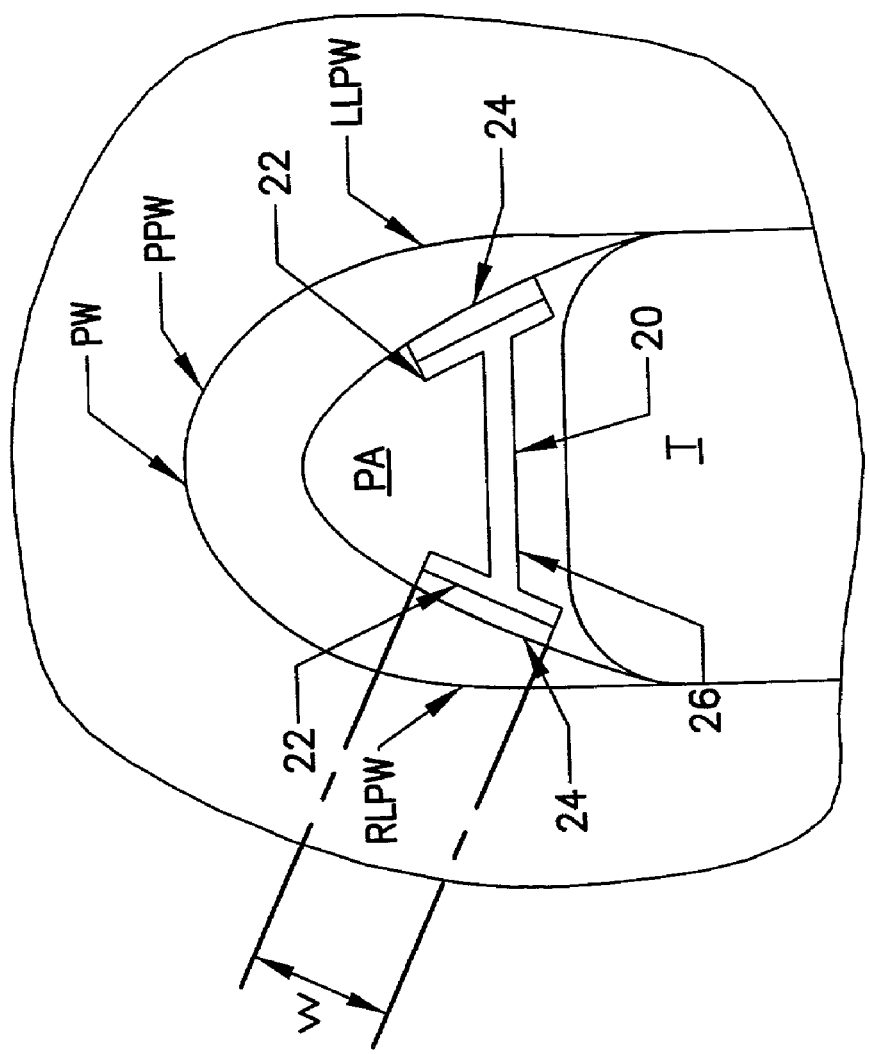
FIG. 6 is the view of FIG. 5 with a first embodiment of an expander member in position prior to activation.

FIG. 6 is the view of FIG. 5 showing an expander member 20 positioned within the pharyngeal airway PA for the purpose of treating the pharyngeal wall PW. As will become apparent, the treatment includes enlargement of the pharyngeal airway PA by urging at least portions of the pharyngeal wall PW outwardly. In the embodiment of FIG. 6, the right and left lateral pharyngeal wall portions RLPW, LLPW are being urged outwardly to increase the area of the airway PA.

The expander member 20 includes left and right supports 22 positioned opposing the right and left lateral pharyngeal wall portions RLPW, LLPW. Compression pads 24 are carried on the supports 22 and in direct opposition to the right and left lateral pharyngeal wall portions RLPW, LLPW. The supports 22 are maintained in fixed spaced apart relation by a spacer bar 26.

While not shown in the drawings, the spacer bar 26 can be adjustable to permit a physician to modify the spacing between the supports 22 and to permit narrowing the spacing between the supports 22 to facilitate ease of placement of the expander member 20 in the airway PA at a desired treatment area. Preferably, the pads 24 and supports 22 have a length (distance parallel to the longitudinal axis of the airway PA) greater than a width (distance parallel to the opposing surface of the wall PW as indicated by W in FIG. 6) to treat an extended length of the wall PW. For example, the pads 24 and supports 22 could be about two centimeters long.

Figure 7:
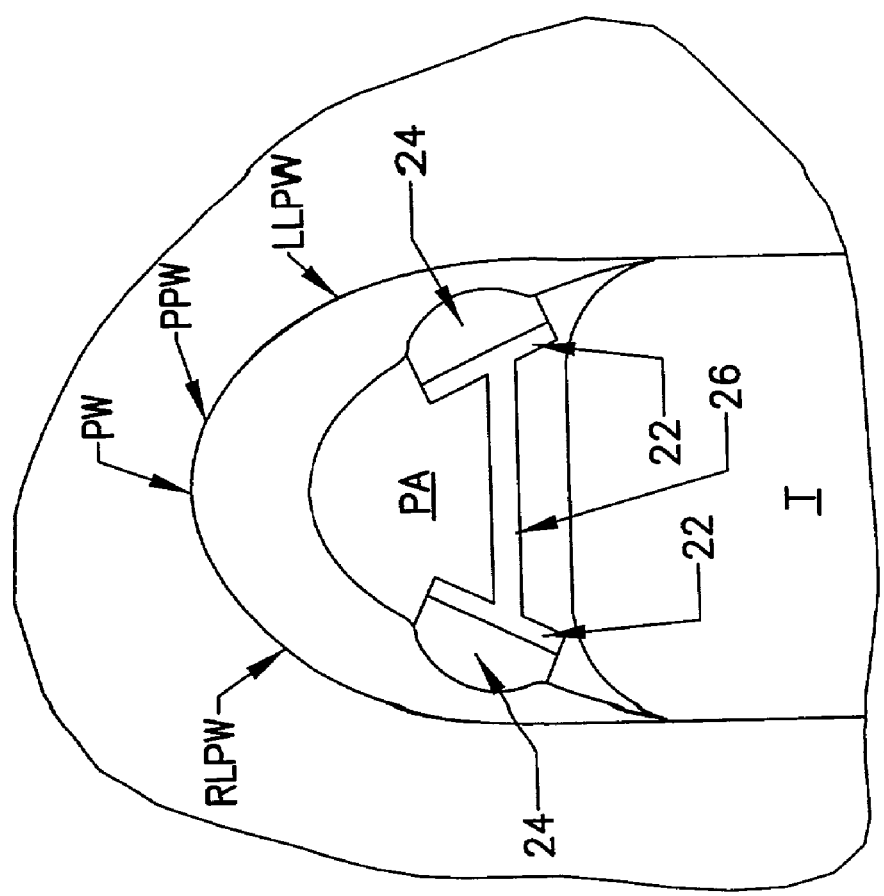
FIG. 7 is the view of FIG. 6 following activation of the expander member to compress portions of the pharyngeal wall.

The compression pads 24 are inflatable bladders connected by a tube 28 (FIG. 8) to a source of a pressurized fluid (not shown). Admission of pressurized fluid into the bladders 24 causes the bladders to enlarge urging the right and left lateral pharyngeal wall portions RLPW, LLPW outwardly as illustrated in FIG. 7. The compression of the tissue of the patient could be compression of the pharyngeal wall PW or compression of tissue surrounding the pharyngeal wall PW (for example, fatty pads). After the compression, the pads 24 are deflated and the expander member 20 is removed from the airway PA as illustrated in FIG. 9 leaving compressed right and left lateral pharyngeal wall portions RLPW, LLPW and an enlarged cross-sectional area of the pharyngeal airway PA.

In addition to compressing the walls of the pharyngeal airway PA, the compressed walls may be stabilized in a compressed state to ensure longer lasting retention of the therapeutic benefits of the enlarged airway PA. This stabilization can include injecting a bio-adhesive or bio-sealants into the tissue adjacent the treated portions of the pharyngeal wall.

An example of bio-adhesives includes cyanoacrylates. Without intending to be a limiting example, these include 2-octyl cyanoacrylate and 2-butyl cyanoacrylate. The 2-octyl cyanoacrylate is developed by Closure Medical Corp., Raleigh, N.C., USA for use to treat topical skin wounds, oral cancers and periodontal disease. It may last 1–2 weeks with faster absorbing products in development. The 2-butyl cyanoacrylate is used as a skin protectant and dental cement and is available from GluStitch, Inc., Delta, BC, Canada Biocompatible adhesives also include surgical adhesives such as those developed by CryoLife International, Inc., Kennesaw, Ga., USA whose product is composed of purified bovine serum albumin (45%) and cross-linking agent glutaraldehyde (10%). Similar formulations include natural proteins (e.g., collagen, gelatin) with aldehyde or other cross-link agents.

Such bio-sealants may be fibrin sealants. Examples include blood-derived products (e.g., Tisseel™ distributed by Baxter Corp., Deerfield, Ill., USA). Other examples of coatings include hydrogel coatings. An example of these include a photocuring synthetic sealant developed by Focal, Inc., Lexington, Mass., USA which can adhere to moist or dry tissue and is highly flexible and elastic. This sealant may be absorbable over short or long terms. The sealant is currently used to treat air leaks associated with lung surgery. Other coatings include denture adhesives approved for use in humans.

From the foregoing, it can be seen there are a wide variety of adhesives and other coatings suitable for use with the present invention. The foregoing lists are intended to be illustrative and not exhaustive.

With the description given with respect to FIGS. 6–9, the bio-stabilizer can be injected into the compressed regions of tissue adjacent the right and left pharyngeal wall. For example, the material can be injected into the compressed portions of the right and left lateral pharyngeal wall portions RLPW, LLPW (mucosal or sub-mucosal or muscular tissue) or into compressed tissue behind the right and left pharyngeal walls, such as compressed fatty tissues. The expander 20 can be left in place while the adhesive as least partially sets such that when the expander 20 is removed, the adhesive helps retain the compressed right and left lateral pharyngeal wall portions RLPW, LLPW in a compressed state.

Bio-adhesives degrade and the therapeutic benefit of the bio-adhesives can be lost over time. Accordingly, a still further embodiment of the present invention includes injecting a fibrosis-inducing agent into the compressed tissue. The fibrosis-inducing agent induces a fibrotic response of the tissue to stiffen the tissue and helping to retain the tissue in a compressed state.

It will be appreciated that the fibrosis-inducing agent may be used in conjunction with the bio-adhesive or the bio-adhesive and fibrosis-inducing agents can be used separately. In the preferred embodiment the fibrosis-inducing agent will be substantially non-biodegradable so as to provide a long lasting, chronic effect maintaining the compressed state of the pharyngeal wall PW.

By way of non-limiting example, a fibrosis-inducing material may be microbeads as described above. While microbeads may be a preferred embodiment, alternative techniques for inducing fibrosis can be in the form of placement in the compressed tissue of polyester material or other foreign bodies which induce a fibrotic response.

In addition to the adhesives or fibrosis-inducing agents, drugs may be admitted into the tissue. Drugs may be injected directly or in microspheres.

Figure 8:
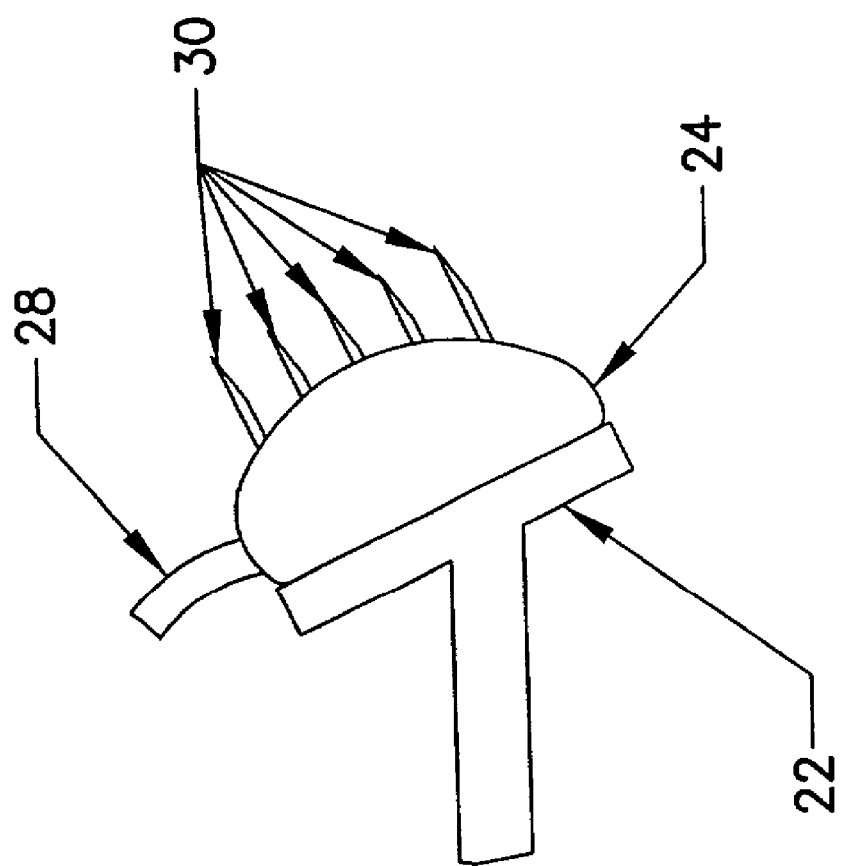
FIG. 8 is a side-sectional view of compression pads used in the expander member of FIG. 7.
Figure 9:
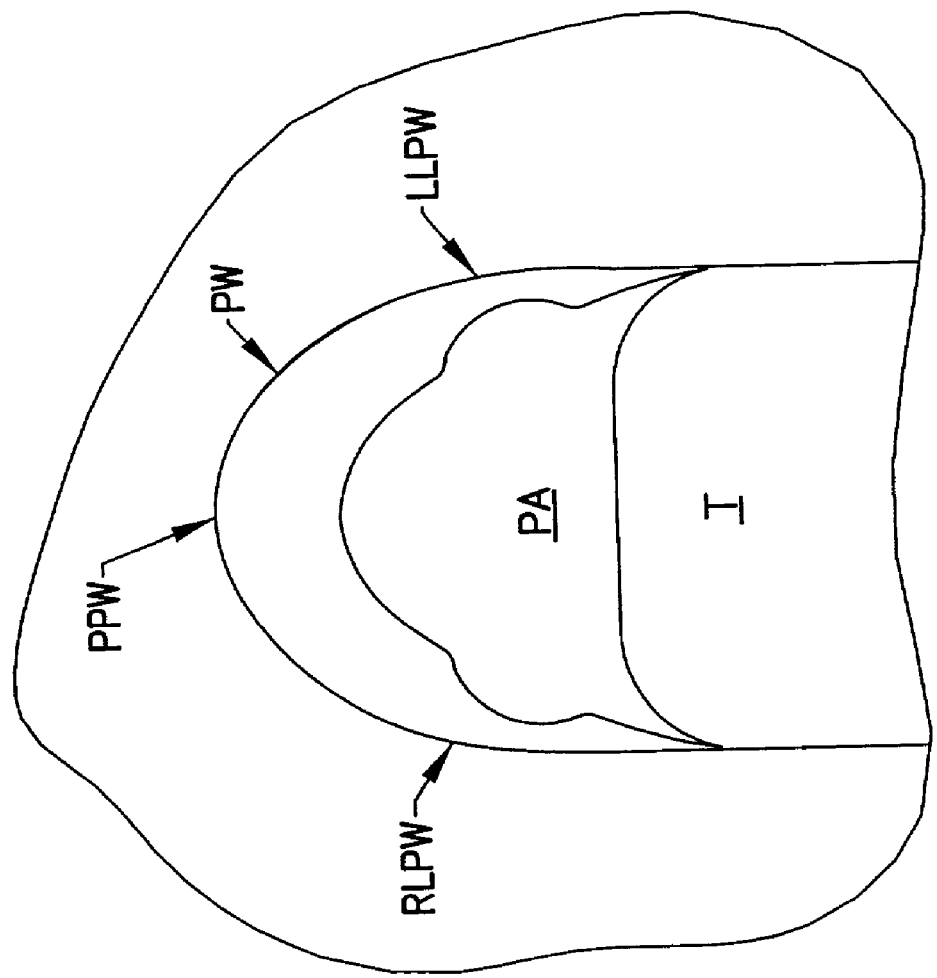
FIG. 9 is the view of FIG. 7 following deactivation and removal of the expander member and showing retention of the pharyngeal wall in an expanded state.

FIG. 8 illustrates an embodiment for injecting adhesives or microbeads into the compressed tissue by the use and placement of micro needles 30 on a side of the bladder 24 opposing the tissue similar to the embodiment of FIG. 4. The fluid from the bladder 24 through the needles 30 contains the bio-adhesives and the microbeads. The micro needles 30 can be of various lengths to vary the depth of distribution of the adhesives and the microbeads.

Figure 10:
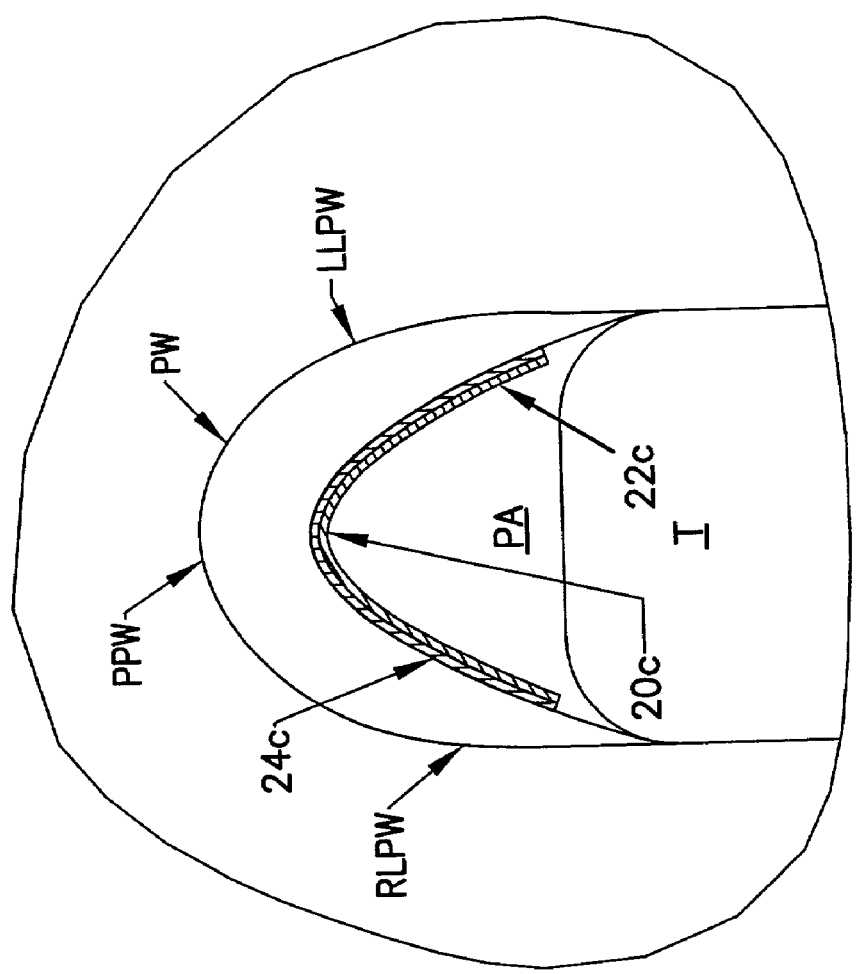
FIG. 10 is the view of FIG. 6 showing an alternative embodiment of the invention.
Figure 11:
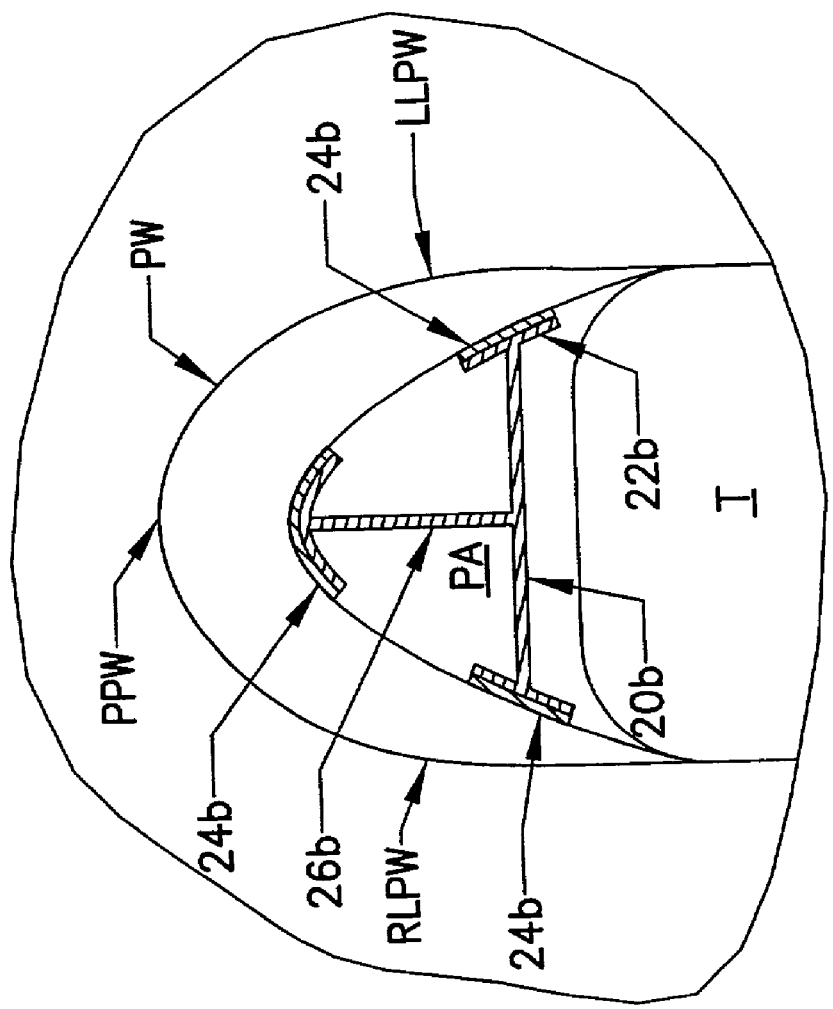
FIG. 11 is the view of FIG. 6 showing a further alternative embodiment of the invention.
Figure 12:
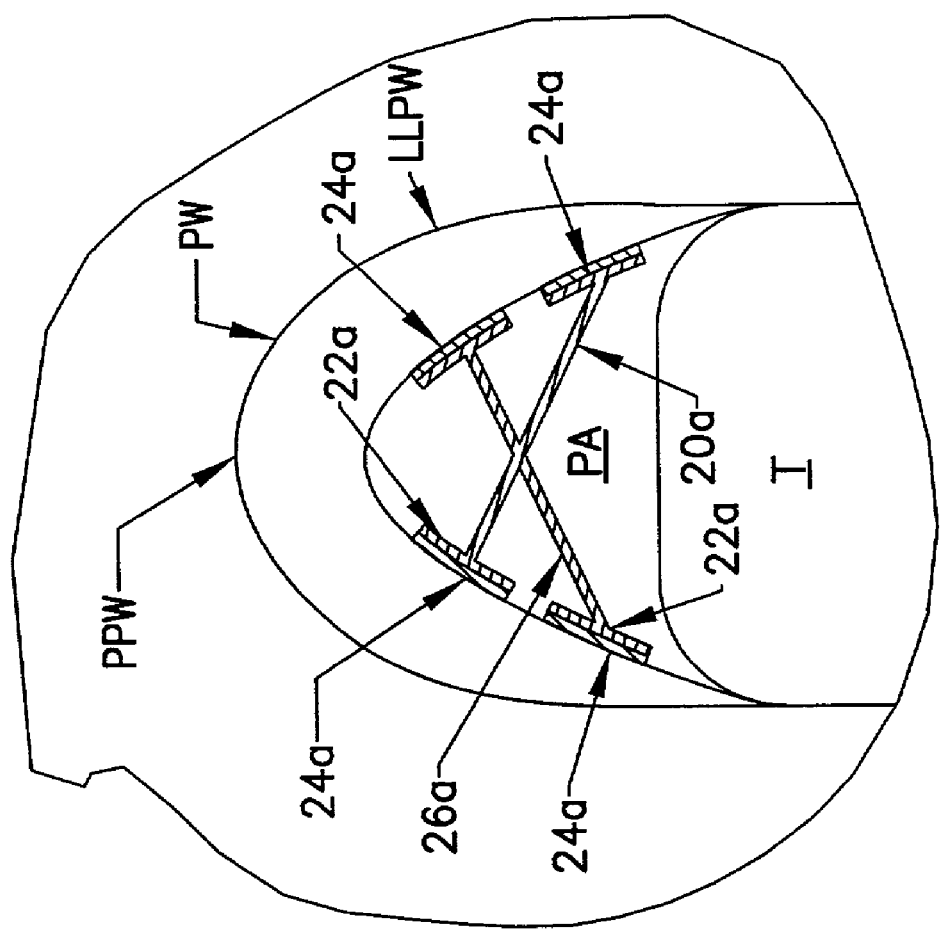
FIG. 12 is the view of FIG. 6 showing a still further alternative embodiment of the invention.

FIGS. 10–12 show alternative embodiments of the present invention. Elements having functions in common with the fore-going embodiment are numbered identically with the addition of a suffix ("a", "b" or "c") to distinguish the embodiments.

In FIGS. 6 and 7, compression members 24 are shown only opposing the right and left lateral pharyngeal wall portions RLPW, LLPW. In FIG. 12, four compression members 24a are shown to cover a wider area of the right and left lateral pharyngeal wall portions RLPW, LLPW. In FIG. 11, three compression members 24b are shown for compressing not only the right and left lateral pharyngeal wall portions RLPW, LLPW but also the posterior pharyngeal wall PPW. In FIG. 10, an arcuate and continuous compression member 24c is shown for compressing the entire pharyngeal wall PW.

Figure 13:
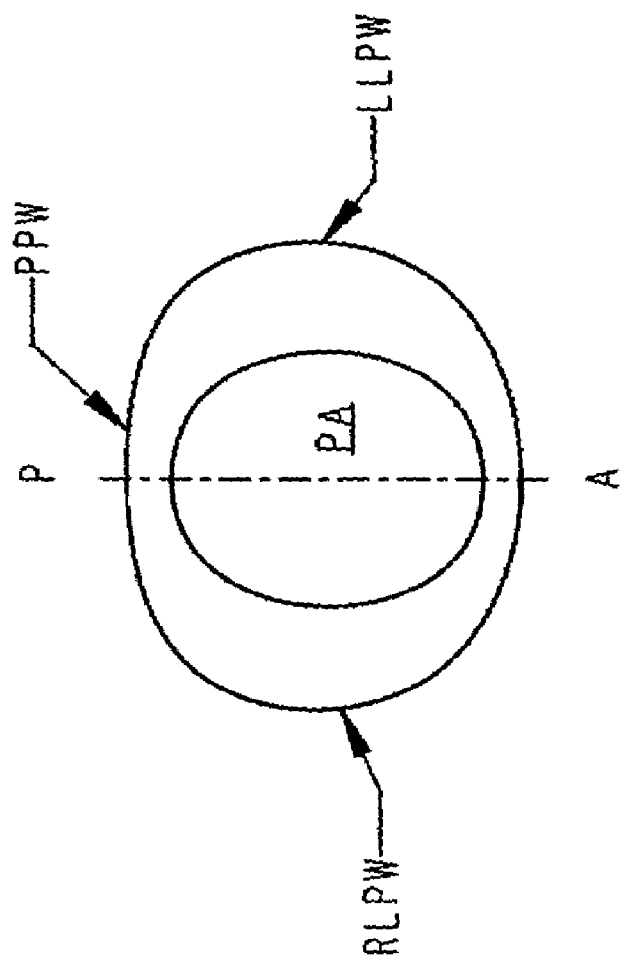
FIG. 13 is a schematic cross-sectional view (taken generally along line 13—13 in FIG. 2) of a pharyngeal airway at a position in a person distal to the base of the tongue and with the airway defined by the pharyngeal wall.
Figure 14:
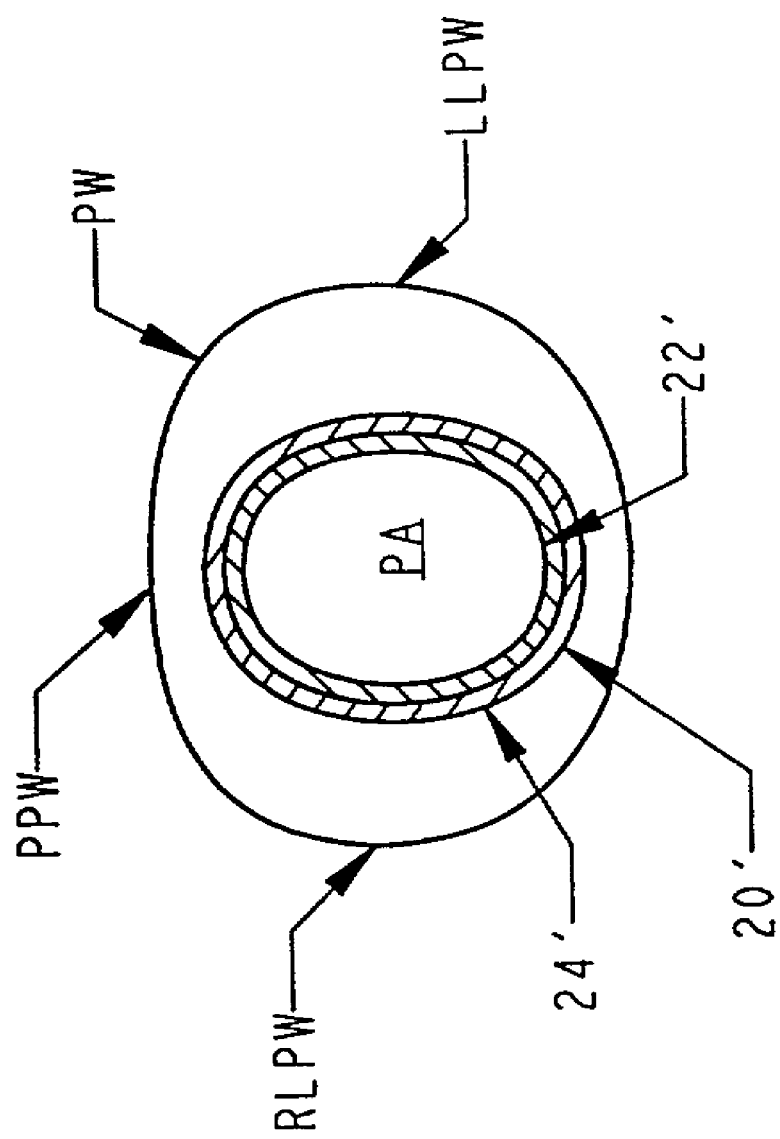
FIG. 14 is the view of FIG. 13 with a further embodiment of an expander member positioned in the airway in a deactivated state.
Figure 15:
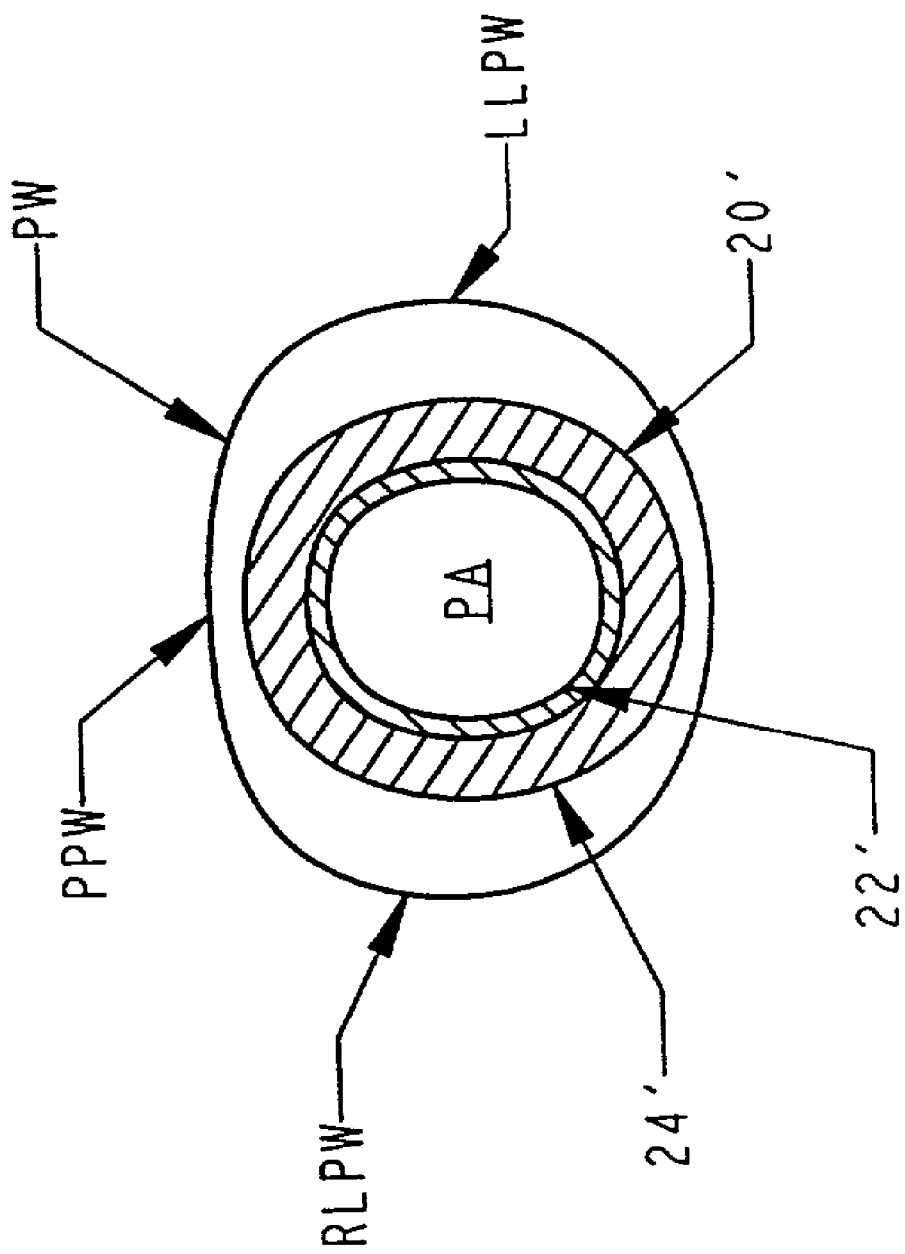
FIG. 15 is the view of FIG. 14 with the expander member shown activated compressing the pharyngeal wall.

FIGS. 13–15 illustrate use of the method of the present invention in a different region of the pharyngeal airway PA. With respect to FIGS. 6–12, the embodiments of the invention are shown in use in that portion of the pharyngeal airway PA which is defined in part by the base of the tongue T. Further distal into the pharyngeal airway PA, the pharyngeal airway PA is defined by the pharyngeal wall PW as illustrated in FIG. 13. The present invention is also applicable to treatment of the naso-pharynx NP (FIG. 1) in which case the airway is defined by lateral and posterior pharyngeal walls and opposing surfaces of the palate. Since this is similar to the shown applications, separate illustrations need not be provided.

Figure 16:
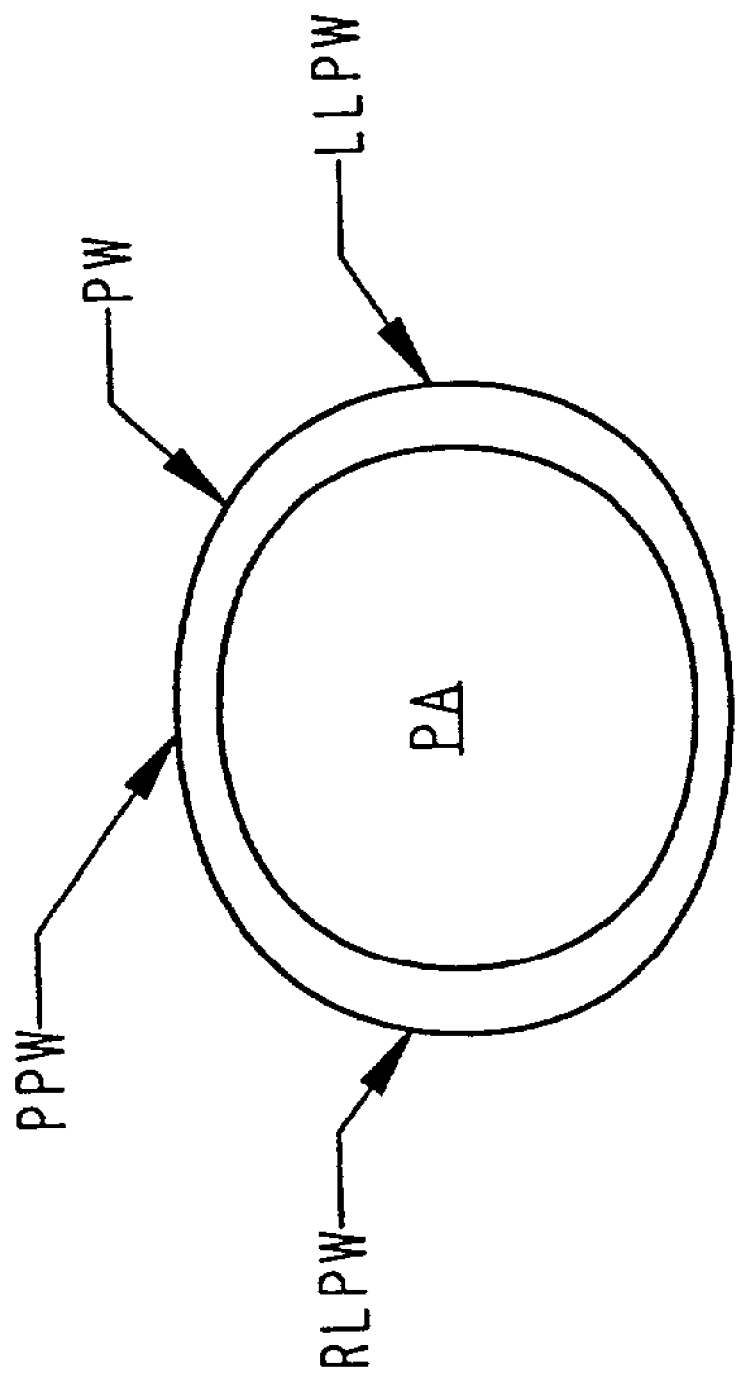
FIG. 16 is the view of FIG. 15 following deactivation and removal of the expander member and showing retention of the pharyngeal wall in an expanded state.

FIG. 14 shows a circular airway expander member 20' having a circular support 22' and a circular bladder 24'. Since the support 22' is annular-shaped, an unobstructed airway PA remains to permit respiration by the patient during treatment. FIG. 15 shows the device with the bladder 22' in an expanded state to cause compression of the pharyngeal wall PW. FIG. 16 shows the compressed pharyngeal wall following removal of the expander member 20'.

Figure 17:
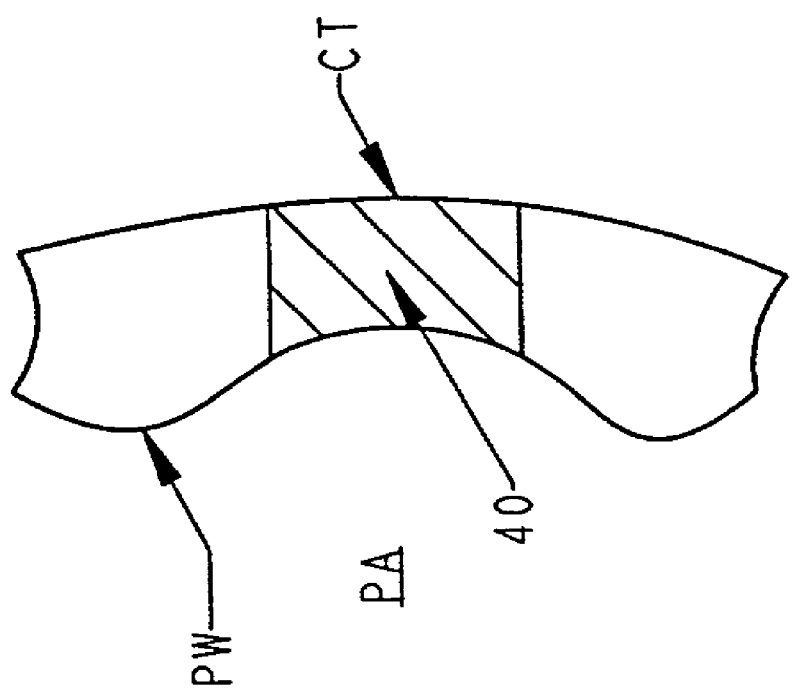
FIG. 17 is a sectional schematic view of a compressed portion of tissue defining, in part, a pharyngeal airway and stabilized by a biocompatible material in the tissue of the compressed portion.

FIGS. 17–22 illustrate various examples of techniques for stabilizing the pharyngeal wall PW. FIG. 17 illustrates a region of compressed tissue CT impregnated with a stabilizing material 40 (e.g., adhesive, sealant or microbeads).

The compressed tissue CT may be compressed mucosal tissue or may be compressed muscular tissue. Also, the compressed tissue CT may be compressed fatty pads adjacent the pharyngeal wall PW.

Stabilization could result from a chemical agent (e.g., a sclerosing agent) or by application of energy (e.g., radiofrequency ablation) or any other means (e.g., cryogenic ablation). It will be appreciated that not all of these techniques need provide a permanent stabilization and some of these techniques may result in remodeling over time. Subsequent treatments may then be provided.

Figure 18:
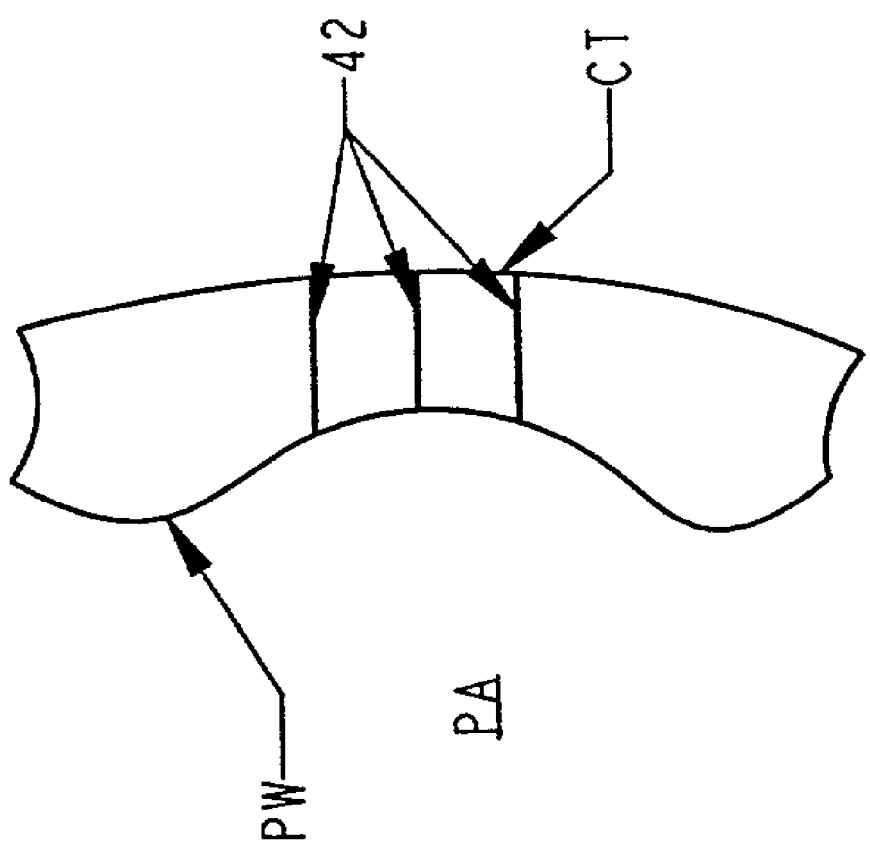
FIG. 18 is the view of FIG. 17 with the compressed tissue stabilized by suture material.
Figure 19:
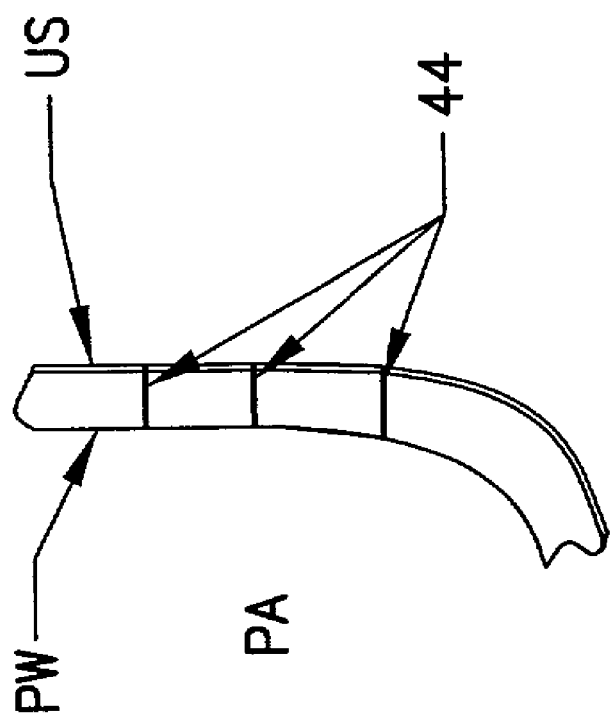
FIG. 19 is the view of FIG. 17 but with the tissue not being compressed and being stabilized by a suture material.

FIG. 18 illustrates a mechanical stabilization using suture material 42 to hold the compressed tissue in a compressed state. The suture material may be resorbable or non-resorbable. FIG. 19 is similar to FIG. 18 but the pharyngeal wall is not compressed. Instead, the pharyngeal wall is stabilized by sutures 44 to underlying structure US (e.g., to underlying bucco-pharyngeal fascia, prevertebral fascia, anterior longitudinal ligament or vertebral bodies). Attachment to such bodies may also occur following compression. Stabilization can result from tacking to any sub-mucosal area surrounding the pharyngeal airway.

Figure 20:
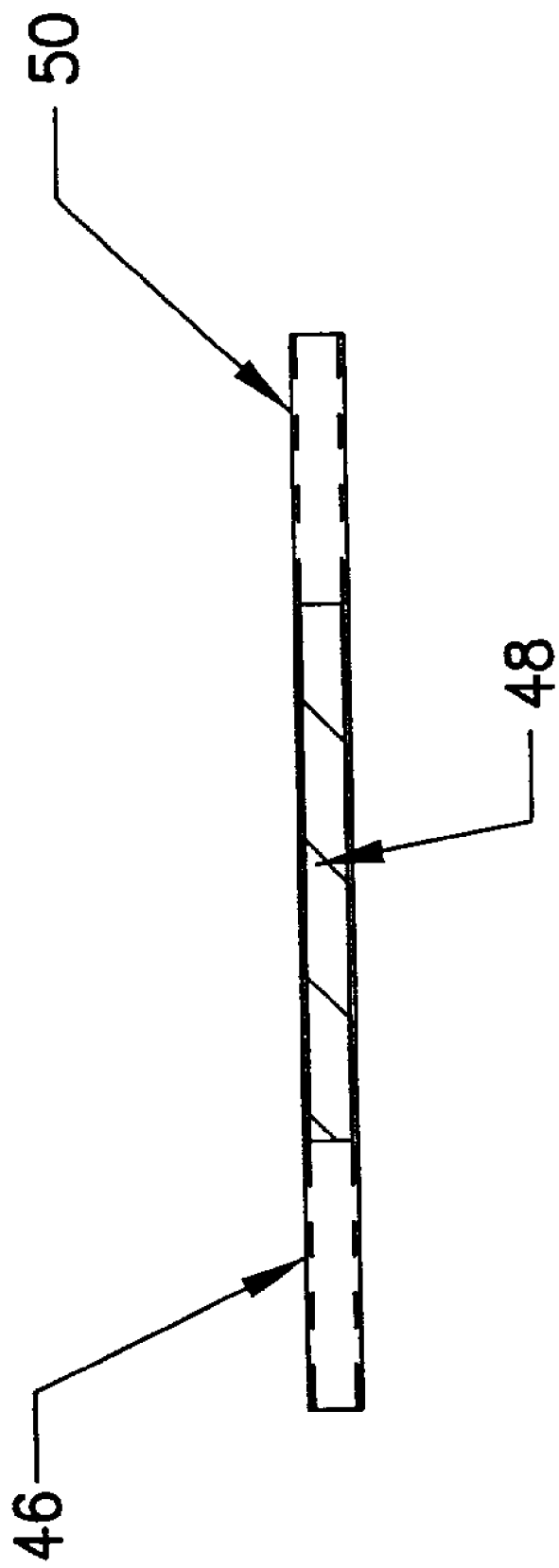
FIG. 20 is a side-sectional schematic view of a suture material having resorbable and non-resorbable portions.
Figure 21:
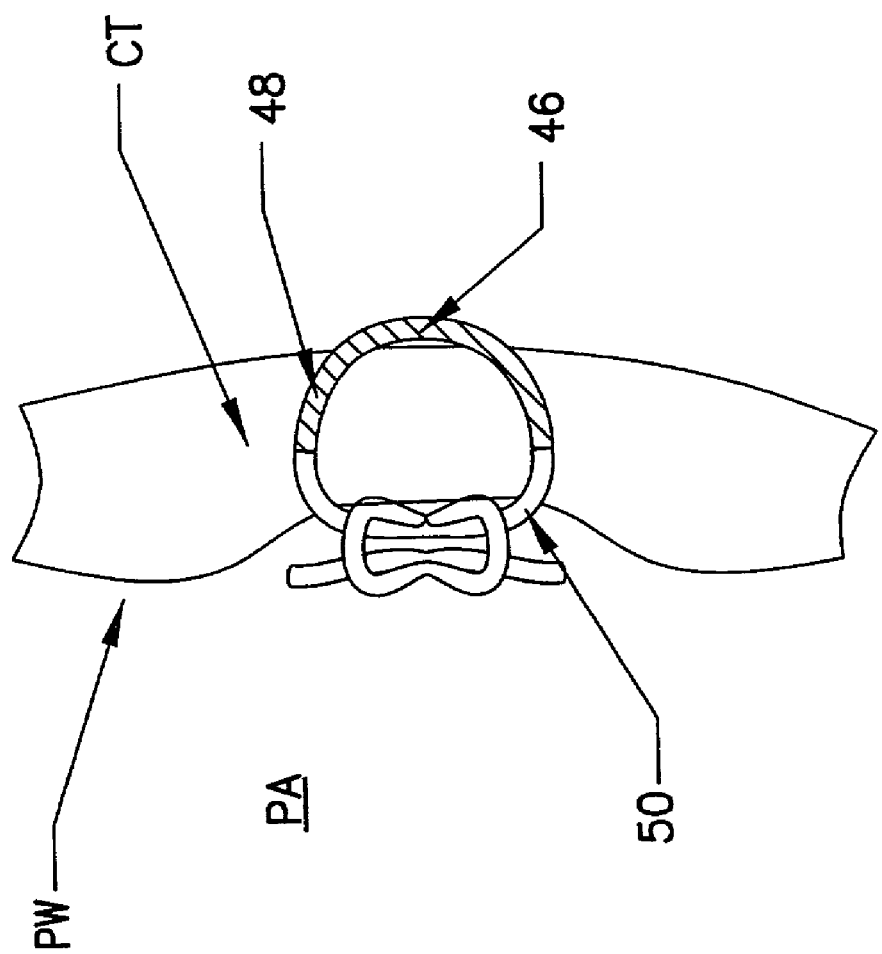
FIG. 21 is the view of FIG. 18 with the suture material of FIG. 20 prior to resorption of the resorbable portions of the suture material.
Figure 22:
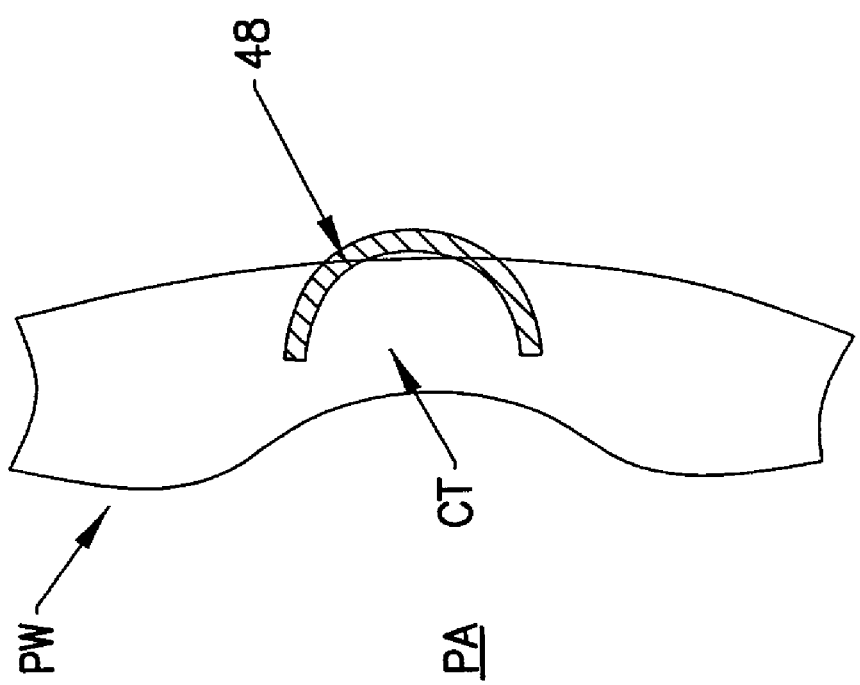
FIG. 22 is the view of FIG. 21 with the suture material of FIG. 20 following resorption of the resorbable portions of the suture material.

FIGS. 20–22 illustrate a variation of FIG. 18 where the suture material 46 includes a short non-resorbable core 48 (e.g., poly ester tetrapthalate—PET) covered by a longer outer coating 50 of resorbable suture material. Immediately after the implantation, only the resorbable ends extend out of the pharyngeal wall PW into the airway PA and are tied off (see FIG. 21). Following resorption, the non-resorbable portion 48 is fully recessed behind the wall PW as shown in FIG. 22 to limit possibility of later migration of the non-resorbable core 48 into the airway PA. In the foregoing, the term "suture" is not intended to be limited to a thread-like material but can include clips or any other closure mechanism.

The foregoing describes numerous embodiments of a method and apparatus to treat a pharyngeal wall. Having described the invention, alternatives and embodiments may occur to one of skill in the art. For example, a physician may stabilize all or a portion of the pharyngeal wall within the teachings of the foregoing with conventional surgical instruments. It is intended that such modifications and equivalents shall be included within the scope of the following claims.

What is claimed is:

1. A method for treating a pharyngeal airway having a pharyngeal wall of a patient at least partially surrounding and defining said airway, said method comprising:
    inserting an expander member into said airway and positioning an active portion of said expander member in an interior of said airway and external to a tissue of said pharyngeal wall and in opposition to an airway-defining tissue of portions of said wall to be treated;
    activating said expander member to urge against said airway-defining tissue of said portions to urge said portions to an outwardly displaced position;
    deactivating said expander member while leaving said portions in said outwardly placed position;
    removing said expander member from said airway; and
    wherein said activating of said expander member creates an area of compressed tissue of said patient adjacent said portions and said method further comprising injecting a biocompatible tissue stabilizer into said compressed tissue while said portions are in said outwardly placed positions.

2. A method according to claim 1 wherein said tissue stabilizer is an adhesive and said removing of said expander member occurs after at least initial setting of said adhesive.

3. A method according to claim 1 wherein said tissue stabilizer is a fibrosis-inducing agent and said injecting includes injecting a said fibrosis-inducing agent into said compressed tissue to induce a fibrotic response from said compressed tissue.

4. A method according to claim 2 wherein said fibrosis-inducing agent is substantially non-biodegradable for said agent to induce a chronic fibrotic response.

5. A method according to claim 4 wherein said fibrosis-inducing agent is a bolus of particulate material.

6. A method for treating a pharyngeal airway having a pharyngeal wall of a patient at least partially surrounding and defining said airway, said method comprising:
    inserting an expander member into said airway and positioning an active portion of said expander member in an interior of said airway and external to a tissue of said pharyngeal wall and in opposition to an airway-defining tissue of portions of said wall to be treated;
    activating said expander member to urge against said airway-defining tissue of said portions to urge said portions to an outwardly displaced position;
    deactivating said expander member while leaving said portions in said outwardly placed position;
    removing said expander member from said airway; and
    injecting a fibrosis-inducing agent into said compressed tissue to induce a fibrotic response from said compressed tissue.

7. A method according to claim 6 wherein said fibrosis-inducing agent is substantially non-biodegradable for said agent to induce a chronic fibrotic response.

8. A method according to claim 7 wherein said fibrosis-inducing agent is a bolus of particulate material.

9. An apparatus for treating a pharyngeal airway having a pharyngeal wall of a patient at least partially surrounding and defining said airway, said method comprising;
    an expander member dimensioned so as to be inserted into said airway with an active portion of said expander member positioned in an interior of said airway and external to a tissue of said pharyngeal wall and in opposition to an airway-defining tissue of portions of said wall to be treated;
    an activator for activating said expander member to urge against said airway-defining tissue of said portions to urge said portions an outwardly displaced position;
    said expander member adapted to be deactivated while leaving said portions in said outwardly placed position;
    said expander member further dimensioned so as to be removable from said airway; and
    an injector for injecting a fibrosis-inducing agent into compressed tissue adjacent said portions while said portions are in said outwardly placed positions.

10. An apparatus according to claim 9 wherein said fibrosis-inducing agent is substantially non-biodegradable.

11. An apparatus according to claim 10 wherein said expander member carries a bolus of a particulate material as said fibrosis-inducing agent.

12. A method for treating a pharyngeal airway having a pharyngeal wall of a patient at least partially surrounding and defining said airway, said method comprising:
    stabilizing at least a portion of said pharyngeal wall against underlying structure by securing said portion of said pharyngeal wall to said structure to resist inward collapse of said pharyngeal wall, where said portion extends transverse to an axis of the airway at least partially surrounding the airway; and
    wherein said stabilization includes accessing said portion through said pharyngeal airway and mechanically securing said portion to said structure;
    wherein said stabilization includes suturing said portion to said structure.

13. A method for treating a pharyngeal airway having a pharyngeal wall of a patient at least partially surrounding and defining said airway, said method comprising:
    accessing at least a portion of a tissue of said pharyngeal wall through said pharyngeal airway, where said portion extends transverse to an axis of the airway at least partially surrounding the airway; and
    compressing said portion to a compressed state;
    stabilizing said portion of said tissue in said compressed state;
    wherein said stabilization includes mechanically securing said portion to a structure underlying said wall; and
    wherein said stabilization includes suturing said portion to a structure underlying said wall.

\* \* \* \* \*